(12) United States Patent
Landau et al.

(10) Patent No.: US 7,744,563 B2
(45) Date of Patent: Jun. 29, 2010

(54) NEEDLE-FREE INJECTION DEVICES AND DRUG DELIVERY SYSTEMS THEREFOR

(75) Inventors: Sergio Landau, Laguna Niguel, CA (US); Daniel E. Williamson, Sherwood, OR (US)

(73) Assignee: Bioject, Inc., Tualatin, OR (US)

( * ) Notice: Subject to any disclaimer, the term of this patent is extended or adjusted under 35 U.S.C. 154(b) by 128 days.

(21) Appl. No.: 12/036,919

(22) Filed: Feb. 25, 2008

(65) Prior Publication Data

US 2008/0208114 A1  Aug. 28, 2008

Related U.S. Application Data

(60) Provisional application No. 60/891,466, filed on Feb. 23, 2007.

(51) Int. Cl.
*A61M 5/30* (2006.01)
(52) U.S. Cl. .......................................... 604/68; 604/71
(58) Field of Classification Search ................... 604/69, 604/71, 68, 110, 111
See application file for complete search history.

(56) References Cited

U.S. PATENT DOCUMENTS

| | | | |
|---|---|---|---|
| 2,545,017 A | 3/1951 | Billingsley |
| 2,582,818 A | 1/1952 | Coby |
| 2,653,602 A | 9/1953 | Smoot |
| 2,667,874 A | 2/1954 | Dickinson, Jr. |
| 2,680,439 A | 6/1954 | Sutermeister |
| 3,110,309 A | 11/1963 | Higgins |
| 3,115,133 A | 12/1963 | Morando |
| 3,202,151 A | 8/1965 | Kath |
| 3,292,621 A | 12/1966 | Banker |

(Continued)

FOREIGN PATENT DOCUMENTS

EP   0427457   5/1991

(Continued)

OTHER PUBLICATIONS

"Zogenix Intraject® Webpage," Copyright 2007, at http://www.zogenix.com/products.html, printed Feb. 12, 2007.

(Continued)

*Primary Examiner*—Nicholas D Lucchesi
*Assistant Examiner*—Leah Stohr
(74) *Attorney, Agent, or Firm*—Kolisch Hartwell, P.C.

(57) ABSTRACT

Needle-free injection devices and drug delivery systems are disclosed. The needle-free injection devices may include a drug delivery system, a power source, an activation system, and a disabling element. The drug delivery system may include a needle-free syringe and a drug storage system. The needle-free syringe may include a plunger slidably disposed within an injection chamber. The injection chamber may include an injection orifice, and the plunger may be configured to expel a volume of fluid from the injection chamber through the injection orifice. The drug storage system may include a storage chamber and an outlet. The drug storage system may be frangibly connected to the needle-free syringe with the outlet proximate to and fluidly connected with the injection orifice. The drug storage system may be configured to inject a fluid from the storage chamber through the outlet, through the injection orifice, and into the injection chamber.

15 Claims, 7 Drawing Sheets

U.S. PATENT DOCUMENTS

| | | |
|---|---|---|
| 3,507,276 A | 4/1970 | Burgess |
| 3,552,083 A | 1/1971 | Andersen et al. |
| 3,561,443 A | 2/1971 | Banker |
| 3,688,765 A | 9/1972 | Gasaway |
| 3,695,266 A | 10/1972 | Lussier |
| 3,714,943 A | 2/1973 | Yanof et al. |
| 3,729,031 A | 4/1973 | Baldwin |
| 3,853,125 A | 12/1974 | Clark et al. |
| 3,859,996 A | 1/1975 | Mizzy et al. |
| 3,940,003 A | 2/1976 | Larson |
| 3,941,128 A | 3/1976 | Baldwin |
| 3,945,379 A | 3/1976 | Pritz et al. |
| 4,059,107 A | 11/1977 | Iriguchi et al. |
| 4,124,024 A | 11/1978 | Schwebel et al. |
| 4,266,541 A | 5/1981 | Landau |
| 4,447,225 A | 5/1984 | Taff et al. |
| 4,479,801 A | 10/1984 | Cohen |
| 4,560,377 A | 12/1985 | Geat et al. |
| 4,592,745 A | 6/1986 | Rex et al. |
| 4,596,556 A | 6/1986 | Morrow et al. |
| 4,652,261 A | 3/1987 | Mech et al. |
| 4,662,878 A | 5/1987 | Lindmayer |
| 4,680,027 A * | 7/1987 | Parsons et al. ............... 604/68 |
| 4,713,061 A | 12/1987 | Tarello et al. |
| 4,717,384 A | 1/1988 | Waldeisen |
| 4,747,839 A | 5/1988 | Tarello et al. |
| 4,790,824 A | 12/1988 | Morrow et al. |
| 4,850,967 A | 7/1989 | Cosmai |
| 4,886,495 A | 12/1989 | Reynolds |
| 4,909,794 A | 3/1990 | Haber et al. |
| 4,913,699 A * | 4/1990 | Parsons ........................ 604/68 |
| 4,940,460 A | 7/1990 | Casey et al. |
| 4,941,880 A | 7/1990 | Burns |
| 5,009,637 A | 4/1991 | Newman et al. |
| 5,024,656 A | 6/1991 | Gasaway et al. |
| 5,049,128 A | 9/1991 | Duquette |
| 5,064,413 A | 11/1991 | McKinnon |
| 5,080,648 A | 1/1992 | D'Antonio |
| 5,135,514 A | 8/1992 | Kimber |
| 5,171,214 A | 12/1992 | Kolbert et al. |
| 5,179,024 A | 1/1993 | Dahms |
| 5,181,909 A | 1/1993 | McFarlane |
| 5,254,086 A * | 10/1993 | Palmer et al. ................ 604/38 |
| 5,273,544 A | 12/1993 | Van der Wal |
| 5,306,277 A | 4/1994 | Bryant et al. |
| 5,318,522 A | 6/1994 | D'Antonio |
| 5,334,144 A | 8/1994 | Alchas et al. |
| 5,364,386 A | 11/1994 | Fukuoka et al. |
| 5,383,851 A | 1/1995 | McKinnon, Jr. et al. |
| 5,393,497 A | 2/1995 | Haber et al. |
| 5,399,163 A | 3/1995 | Peterson et al. |
| 5,453,096 A | 9/1995 | Lataix |
| 5,462,535 A | 10/1995 | Bonnichsen et al. |
| 5,472,022 A | 12/1995 | Michel et al. |
| 5,480,381 A | 1/1996 | Weston |
| 5,499,972 A | 3/1996 | Parsons |
| 5,503,627 A | 4/1996 | McKinnon et al. |
| 5,503,628 A | 4/1996 | Fetters et al. |
| 5,505,697 A | 4/1996 | McKinnon, Jr. et al. |
| 5,520,639 A | 5/1996 | Peterson et al. |
| 5,569,190 A | 10/1996 | D'Antonio |
| 5,573,513 A | 11/1996 | Wozencroft |
| 5,599,302 A | 2/1997 | Lilley et al. |
| 5,645,538 A | 7/1997 | Richmond |
| 5,704,911 A | 1/1998 | Parsons |
| 5,716,348 A | 2/1998 | Marinacci et al. |
| 5,730,723 A | 3/1998 | Castellano et al. |
| 5,746,714 A | 5/1998 | Salo et al. |
| 5,769,138 A | 6/1998 | Sadowski et al. |
| 5,782,802 A | 7/1998 | Landau |
| 5,865,795 A | 2/1999 | Schiff et al. |
| 5,891,085 A | 4/1999 | Lilley et al. |
| 5,891,086 A | 4/1999 | Weston |
| 5,893,397 A | 4/1999 | Peterson et al. |
| 5,911,703 A | 6/1999 | Slate et al. |
| 5,921,967 A | 7/1999 | Sadowski et al. |
| 5,938,637 A | 8/1999 | Austin et al. |
| 5,957,886 A | 9/1999 | Weston |
| 5,993,412 A | 11/1999 | Deily |
| 6,053,890 A | 4/2000 | Moreau Defarges et al. |
| 6,056,716 A | 5/2000 | D'Antonio et al. |
| 6,063,053 A | 5/2000 | Castellano et al. |
| 6,080,130 A | 6/2000 | Castellano |
| 6,096,002 A | 8/2000 | Landau |
| 6,132,395 A | 10/2000 | Landau et al. |
| 6,135,979 A | 10/2000 | Weston |
| 6,149,625 A | 11/2000 | Weston et al. |
| 6,156,008 A | 12/2000 | Castellano |
| 6,168,587 B1 | 1/2001 | Bellhouse et al. |
| 6,174,304 B1 | 1/2001 | Weston |
| 6,179,583 B1 | 1/2001 | Weston |
| 6,210,359 B1 | 4/2001 | Patel et al. |
| 6,216,493 B1 * | 4/2001 | Weston et al. .................. 65/68 |
| 6,223,786 B1 | 5/2001 | Castellano |
| 6,224,567 B1 | 5/2001 | Roser |
| 6,251,091 B1 | 6/2001 | Weston |
| 6,251,099 B1 | 6/2001 | Kollias et al. |
| 6,258,059 B1 | 7/2001 | Weston et al. |
| 6,264,629 B1 | 7/2001 | Landau |
| 6,280,410 B1 | 8/2001 | Weston et al. |
| 6,319,224 B1 | 11/2001 | Stout et al. |
| 6,383,168 B1 | 5/2002 | Landau et al. |
| 6,387,074 B1 | 5/2002 | Horppu et al. |
| 6,406,455 B1 | 6/2002 | Willis et al. |
| 6,409,032 B1 | 6/2002 | Bekkers et al. |
| 6,415,631 B1 | 7/2002 | Weston et al. |
| 6,471,669 B2 | 10/2002 | Landau |
| 6,475,181 B1 | 11/2002 | Potter et al. |
| 6,537,245 B1 | 3/2003 | Alexandre et al. |
| 6,554,818 B2 | 4/2003 | Weston et al. |
| 6,558,348 B2 | 5/2003 | Parsons |
| 6,572,581 B1 | 6/2003 | Landau |
| 6,585,685 B2 | 7/2003 | Staylor et al. |
| 6,607,510 B2 | 8/2003 | Landau |
| 6,610,028 B1 | 8/2003 | Alexandre et al. |
| 6,616,627 B2 | 9/2003 | Willis et al. |
| 6,620,135 B1 | 9/2003 | Weston et al. |
| 6,623,446 B1 | 9/2003 | Navelier et al. |
| 6,623,449 B2 | 9/2003 | Paskar |
| 6,641,554 B2 | 11/2003 | Landau |
| 6,645,170 B2 | 11/2003 | Landau |
| 6,648,850 B2 | 11/2003 | Landau |
| 6,652,483 B2 | 11/2003 | Slate et al. |
| 6,666,843 B1 | 12/2003 | Alexandre et al. |
| 6,673,038 B2 | 1/2004 | Weston |
| 6,676,630 B2 | 1/2004 | Landau et al. |
| 6,681,810 B2 | 1/2004 | Weston |
| 6,682,504 B2 | 1/2004 | Nelson et al. |
| 6,689,093 B2 | 2/2004 | Landau |
| 6,752,780 B2 | 6/2004 | Stout et al. |
| 6,752,781 B2 | 6/2004 | Landau et al. |
| 6,758,829 B2 | 7/2004 | Alexandre et al. |
| 6,783,509 B1 | 8/2004 | Landau et al. |
| 6,835,187 B2 | 12/2004 | Alexandre et al. |
| 6,837,866 B1 | 1/2005 | Alexandre et al. |
| 6,883,222 B2 | 4/2005 | Landau |
| 6,905,475 B2 | 6/2005 | Hauschild et al. |
| 6,911,015 B2 | 6/2005 | Alexandre et al. |
| 6,913,593 B1 | 7/2005 | Alexandre et al. |
| 6,935,384 B2 | 8/2005 | Landau et al. |
| 6,939,324 B2 | 9/2005 | Gonnelli et al. |
| 6,942,645 B2 | 9/2005 | Alexandre et al. |
| 6,960,184 B2 | 11/2005 | Willis et al. |
| 6,964,650 B2 | 11/2005 | Alexandre et al. |

| | | |
|---|---|---|
| 6,979,310 B2 | 12/2005 | Navelier et al. |
| 6,981,961 B1 | 1/2006 | Navelier et al. |
| 7,056,300 B2 | 6/2006 | Alexandre et al. |
| 7,150,409 B2 | 12/2006 | Gonnelli et al. |
| 7,156,822 B2 | 1/2007 | Navelier et al. |
| 7,156,823 B2 | 1/2007 | Landau et al. |
| 7,357,780 B2 | 4/2008 | Alexandre et al. |
| 2001/0002433 A1 | 5/2001 | Weston |
| 2001/0004682 A1 | 6/2001 | Weston |
| 2002/0156418 A1 | 10/2002 | Gonnelli et al. |
| 2003/0149397 A9 | 8/2003 | Gonnelli et al. |
| 2003/0187386 A1 | 10/2003 | Parsons |
| 2004/0106895 A1 | 6/2004 | Slate et al. |
| 2004/0111054 A1 | 6/2004 | Landau et al. |
| 2004/0210188 A1 | 10/2004 | Glines et al. |
| 2004/0215136 A1 | 10/2004 | Navelier et al. |
| 2004/0215137 A1 | 10/2004 | Navelier et al. |
| 2004/0220525 A1 | 11/2004 | Willis et al. |
| 2004/0254526 A1 | 12/2004 | Weston |
| 2005/0010167 A1 | 1/2005 | Alexandre et al. |
| 2005/0119618 A1 | 6/2005 | Gonnelli |
| 2005/0154350 A1 | 7/2005 | Willis et al. |
| 2005/0192530 A1 | 9/2005 | Castellano |
| 2005/0209554 A1 | 9/2005 | Landau |
| 2005/0267403 A1 | 12/2005 | Landau et al. |
| 2006/0069345 A1 | 3/2006 | Anderson et al. |
| 2006/0089594 A1* | 4/2006 | Landau ................. 604/68 |
| 2006/0089595 A1 | 4/2006 | Alexandre et al. |
| 2006/0189927 A1 | 8/2006 | Alexandre et al. |
| 2006/0247573 A1 | 11/2006 | Alexandre et al. |

FOREIGN PATENT DOCUMENTS

| | | |
|---|---|---|
| NL | 133435 | 2/1972 |
| WO | 9015633 | 12/1990 |
| WO | WO9737705 | 10/1997 |
| WO | 9813086 | 4/1998 |
| WO | WO9852632 | 11/1998 |
| WO | WO0033899 | 6/2000 |
| WO | WO0048654 | 8/2000 |
| WO | WO0113975 | 3/2001 |
| WO | 0137906 | 5/2001 |
| WO | WO03103752 | 12/2003 |

OTHER PUBLICATIONS

"Zogenix DosePro Webpage," Copyright 2008, at http://www.zogenix.com/index.php/products/sumatriptandosepro/, printed Jul. 9, 2008.

"Schott Ampoules made of Glass Webpage," Copyright 2007, at http://www.us.schott.com/pharmaceutical_packaging/english/products/ampules/index.html, printed Jun. 26, 2007.

"BioValve Mini-Ject Webpage," at http://www.biovalve.com/products/miniject.shtml, printed Feb. 12, 2007.

"Pages from Crossject Website," at http://www.crossject.com/, printed Feb. 12, 2007.

"LMS SureFlo® Technical Data & Drawings," Copyright 2006, from LMS webpage at http://www.lmselastovalves.com/sureflo_tech.html, printed Jul. 9, 2008.

"Vernay® Check Valves: Engineering Fluid Control," Brochure of Vernay Laboratories, Inc., Copyright Jan. 24, 2008.

* cited by examiner

NEEDLE-FREE INJECTION DEVICES AND DRUG DELIVERY SYSTEMS THEREFOR

RELATED APPLICATION

This application claims priority to U.S. Provisional Patent Application Ser. No. 60/891,466, which was filed on Feb. 23, 2007 and is entitled "Enclosed Needle-Free Injector Having Parallel Architecture." The complete disclosure of the above-identified patent application is hereby incorporated by reference for all purposes.

FIELD OF THE DISCLOSURE

The present disclosure relates to needle-free injection systems, devices and components, and more particularly to needle-free injection systems, devices and components for injecting drugs.

BACKGROUND OF THE DISCLOSURE

Needle-free injection systems and devices provide an alternative to standard fluid delivery systems, which generally use a needle adapted to penetrate the outer surface of a target. Typically, needle-free injection systems and devices are designed to eject the fluid from a fluid chamber with sufficient pressure to allow the fluid to penetrate the target to the desired degree. For example, common applications for needle-free injection systems and devices include delivering intradermal, subcutaneous and intramuscular injections into or through a recipient's skin. For each of these applications, the fluid must be ejected from the system or device with sufficient pressure to allow the fluid to penetrate the tough exterior dermal layers of the recipient's skin.

Examples of needle-free injection systems and components therefor are disclosed in U.S. Pat. Nos. 4,940,460; 4,941,880; 5,064,413; 5,383,851; 5,399,163; 5,505,697; 5,520,639; 5,746,714; 5,782,802; 5,891,086; 5,893,397; 5,993,412; 6,096,002; 6,132,395; 6,174,304; 6,251,091; 6,264,629; 6,280,410; 6,319,224; 6,383,168; 6,471,669; 6,554,818; 6,572,581; 6,585,685; 6,607,510; 6,620,135; 6,641,554; 6,645,170; 6,648,850; 6,676,630; 6,689,093; 6,752,780; 6,752,781; 6,783,509; 6,935,384; and 6,964,650; U.S. Pat. App. Pub. Nos. 2001/0051793; 2004/0254526; 2006/0089595; 2006/0189927; 2006/02475733; and U.S. patent application Ser. No. 11/539,585, which was filed Oct. 6, 2006, and titled "TRIGGERING MECHANISM FOR NEEDLE-FREE INJECTOR." The disclosures of these and all other publications referenced herein are incorporated by reference in their entirety for all purposes.

SUMMARY OF THE DISCLOSURE

Needle-free injection devices may include a drug delivery system, a power source, an activation system, and a disabling element or an activation preventing element. The power source may be configured to apply an injection force to the plunger to expel a volume of fluid from the injection chamber through the injection orifice, and the activation system may be configured to selectively cause the power source to apply the injection force.

In some examples, drug delivery systems may include a needle-free syringe and a drug storage system. The needle-free syringe may include an injection chamber and a plunger slidably disposed within the injection chamber. The injection chamber may include an injection orifice. The plunger may be configured to expel the volume of fluid from the injection chamber through the injection orifice. The drug storage system may include a storage chamber and an outlet. The drug storage system may be frangibly connected to the needle-free syringe with the outlet proximate to and fluidly connected with the injection orifice. The drug storage system may be configured to inject a fluid from the storage chamber through the outlet, through the injection orifice, and into the injection chamber.

The disabling element may be configured to prevent the power source from applying the injection force when the drug storage system is frangibly connected to the needle-free syringe. The disabling element may be configured to permit application of the injection force when the drug storage system is disconnected from the needle-free syringe.

In some examples, drug delivery systems may include a needle-free syringe, a drug storage system, and a frangible connector. The needle-free syringe may include an injection chamber and a plunger slidably disposed within the injection chamber. The injection chamber may include an injection orifice and the plunger may be configured to expel a volume of fluid from the injection chamber through the injection orifice. The drug storage system may include a storage chamber and an outlet. The storage chamber may be configured to inject a fluid from the storage chamber through the outlet, through the injection orifice, and into the injection chamber. The frangible connector may be configured to retain the drug storage system proximate the needle-free syringe with the outlet proximate to and fluidly connected with the injection orifice.

The activation preventing element may be configured to prevent the activation system from causing the power source to apply the injection force when the frangible connector is retaining the drug storage system proximate the needle-free syringe. The activation preventing element may be configured to permit the activation system to cause the power source to apply the injection force when the frangible connector has been broken.

Drug delivery systems for needle-free injection devices may include a needle-free syringe, a drug storage system, and a connector. The needle-free syringe may include an injection chamber and an injection plunger slidably disposed within the injection chamber. The injection chamber may include an injection orifice and the injection plunger may be configured to expel a volume of fluid from the injection chamber through the injection orifice. The drug storage system may include a storage chamber, an outlet and an ejection plunger. The ejection plunger may be configured to eject a fluid from the storage chamber through the outlet.

The connector may be configured to retain the drug storage system proximate the needle-free syringe with the outlet proximate the injection orifice. The connector may include a first connecting region, a second connecting region, a fluid path, a valve, and a stress riser. The first connecting region may be configured to retain the connector to the drug storage system proximate the outlet. The second connecting region may be configured to retain the connector to the needle-free syringe proximate the injection orifice. The fluid path may be configured to fluidly connect the outlet and the injection orifice. The valve may be configured to interrupt the fluid path proximate the outlet. The fluid ejected from the storage chamber through the outlet may pass through the valve, through the injection orifice, and into the injection chamber. The stress riser may be configured to assist with separation of the first and second connecting regions and to assist with separation of the drug storage system from the needle-free syringe.

DETAILED DESCRIPTION OF THE DISCLOSURE

A nonexclusive illustrative example of a needle-free injection device is shown generally at 20 in FIGS. 1, 2, 4-6, and 13-20. Unless otherwise specified, needle-free injection device 20 may, but is not required to, contain at least one of the structure, components, functionality, and/or variations described, illustrated, and/or incorporated herein. Although the needle-free injection device 20 may be configured as a single-use, disposable device, the needle-free injection device 20 may also be configured as a reusable and/or refillable device suitable for multiple uses, and at least some of the various components of the needle-free injection device 20 may be suitable for use in or with reusable and/or refillable devices. The needle-free injection device 20 may include a case 22, a drug delivery system 24, a power source 26, an activation system 28, and an activation preventing or disabling element 30.

Figures 1, 2:
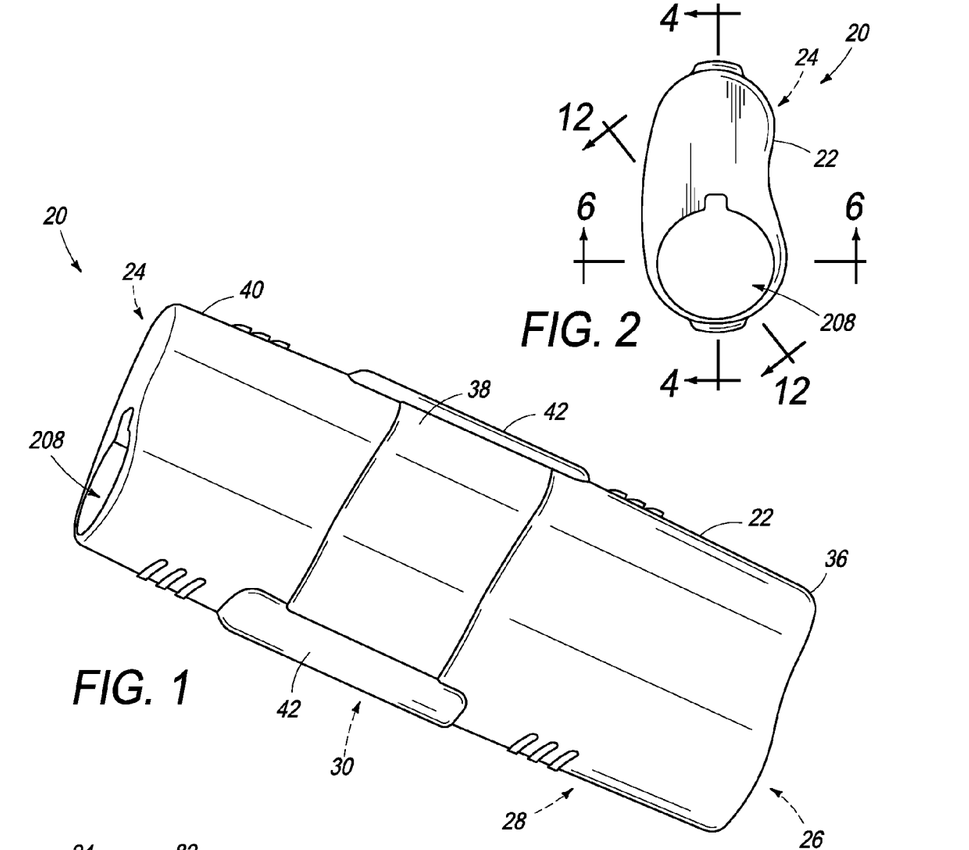
FIG. 1 is a perspective view of an illustrative example of a needle-free injection device in a storage configuration.
FIG. 2 is an end view of the needle-free injection device of FIG. 1.
Figure 4:
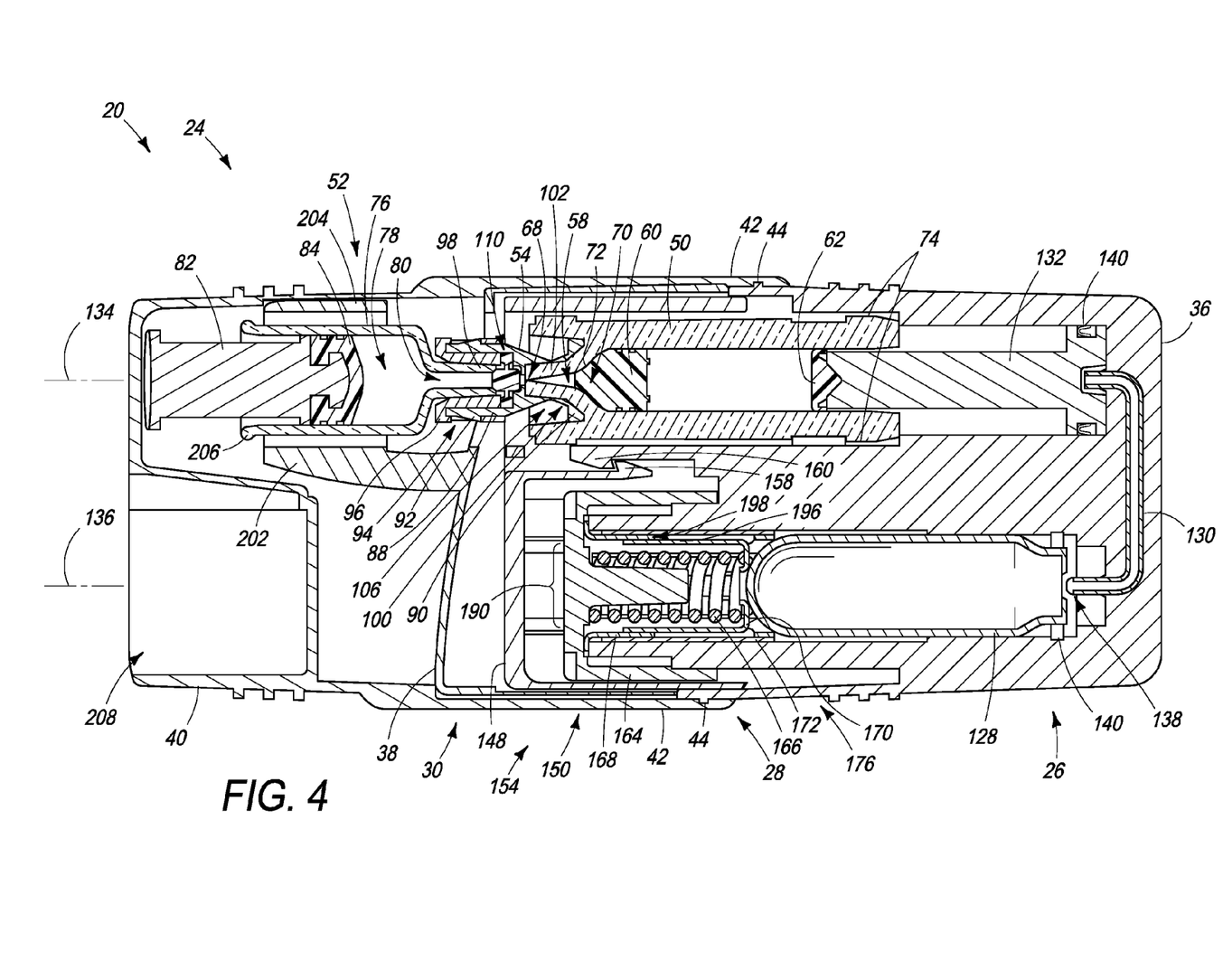
FIG. 4 is a cross section of the needle-free injection device of FIG. 1, taken generally along line 4-4 in FIG. 2, with the needle-free injection device and drug delivery system shown in the storage configuration.
Figure 5:
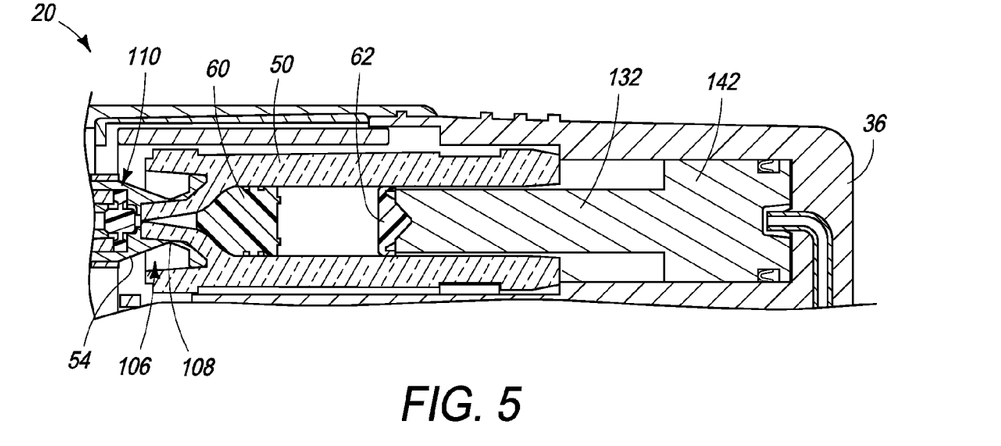
FIG. 5 is a cross section partial view of another illustrative example of a needle-free injection device configured for dispensing a smaller dose of fluid than the needle-free injection device of FIG. 1, taken generally along a line corresponding to line 4-4 in FIG. 2, shown in a storage configuration.

The case 22 may be a generally flattened elongate body, which may be contoured such as to more readily fit into a pocket, as shown in FIGS. 1 and 2. The case 22 may include a main body 36, a shield element 38, and a removable cap 40. The removable cap 40 may be retained relative to the main body 36 via a pair of opposed arms 42, which may engage corresponding detents 44 on the main body 36, as shown in FIG. 4. The various components of the case may be fabricated from a suitable material, such as polycarbonate or another thermoplastic.

Figure 3:
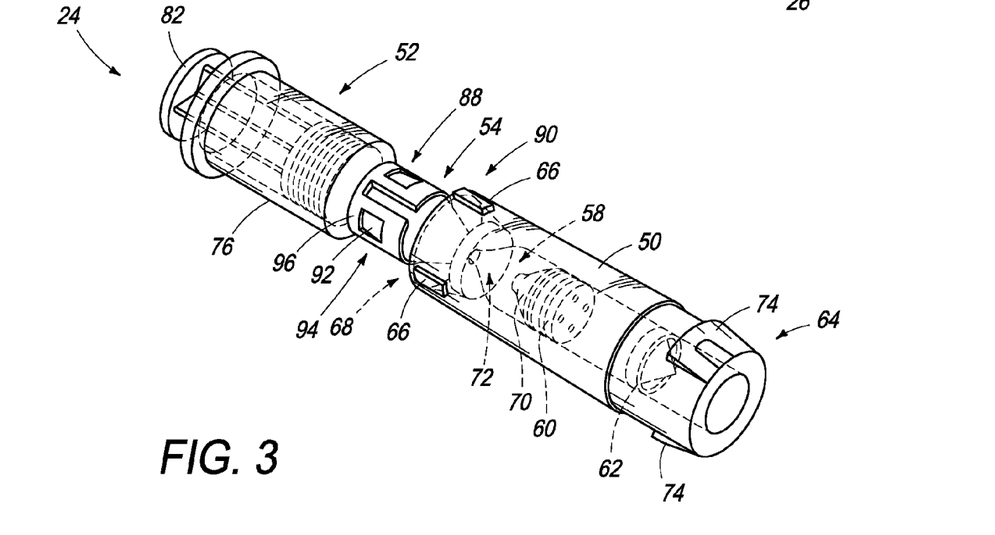
FIG. 3 is a perspective view of an illustrative example of a drug delivery system suitable for use with the needle-free injection device of FIG. 1.

As shown in FIG. 3, the drug delivery system 24 may include a nozzle or needle-free syringe 50 and a drug storage system 52, which may be connected to the needle-free syringe 50 via a connector 54. The word "drug" as used herein is intended to encompass, for example, and without limitation, any medication, pharmaceutical, therapeutic, vaccine, or other material which can be administered by injection.

The needle-free syringe 50 may include an injection chamber 58, an injection plunger 60, a back seal 62, a mounting structure 64, and at least one tool engaging feature 66. The injection chamber 58 may include an injection orifice 68, which may be in the form of a fine-dimension opening from which issues a high velocity jet of medication upon actuation of the device, as will be more fully discussed below. The injection chamber 58 may be sized for delivery of an appropriate volume of fluid or drug, such as 0.5 mL, 1.0 mL, or any other suitable dose size.

The injection plunger 60 may be slidably and sealingly disposed within the injection chamber 58. As shown in FIGS. 3 and 4, the injection plunger 60 may be configured to expel a volume of fluid from the injection chamber 58 through the injection orifice 68. In some examples, the injection plunger 60 may include a contoured tip 70. As shown in FIG. 4, the contoured tip 70 may be configured to closely fit into the end 72 of the injection chamber 58, which may reduce dead volume within the injection chamber 58 and/or more completely permit injection of the volume of fluid within the injection chamber 58.

The back seal 62 may include may be slidably and sealingly disposed within the injection chamber 58, with the injection plunger 60 being disposed between the back seal 62 and the injection orifice 68. The back seal 62 may provide an environmental seal configured to maintain sterility of the injection chamber 58 and the injection plunger 60.

The mounting structure 64 may include any structural features suitable for creating an engagement between the needle-free syringe 50 and the main body 36. The mounting structure may include threads, or as shown in FIGS. 3 and 4, the mounting structure 64 may be in the form of one or more bayonet-type mounting tabs 74 configured to engage a corresponding feature on the main body 36. Use of bayonet-type mounting tabs 74 may permit engagement and disengagement between the needle-free syringe 50 and the main body 36 based on rotation through less than a complete revolution, such as approximately ninety (90) degrees of rotation. Such rotation may be caused or induced by a suitable tool, such as one configured to engage the tool engaging features 66 on the needle-free syringe 50.

As will be more fully discussed below, the illustrative needle-free syringe 50 presented herein may be configured for injection of drugs, without needing to be configured or suitable for long-term storage of the drugs. Thus, the needle-free syringe 50 may be fabricated from a material suitable for resisting the needle-free injection pressures, which may be in excess of 1000 psi, without regard to the suitability of the material for long-term drug storage. For example, the needle-free syringe 50 may be fabricated from a thermoplastic material such as a polycarbonate or other suitable thermoplastic. In some examples, the needle-free syringe 50 may be fabricated from a transparent material.

The drug storage system 52 may be any suitable structure configured to store and subsequently inject a drug or fluid through the injection orifice 68 and into the injection chamber 58 of the needle-free syringe 50. For example, as shown in FIGS. 3 and 4, the drug storage system 52 may be in the form of a syringe 76 that includes a storage vial or chamber 78 having an outlet 80 and an ejection mechanism or plunger 82. As will be more fully discussed below, the plunger 82 may be used to eject a drug or fluid from the storage chamber 78, through the outlet 80, through the injection orifice 68, and into the injection chamber 58.

As the drug storage system 52 presented herein may be configured for long-term storage of drugs, the portions of the drug storage system 52 in contact with the drugs should be compatible with long-term exposure to the drugs. For example, the chamber 78 may be a borosilicate glass syringe, which may be transparent, and the tip 84 of the plunger 82 may be fabricated from chlorobutyl or any other material suitable for drug contact. However, as will be more fully discussed below, the illustrative drug storage system 52 is not exposed to the aforementioned needle-free injection pressures. Rather, the illustrative drug storage system 52 need only withstand filling pressures, which may be on the order of 100 psi or less, such that a standard borosilicate syringe, as known in the art, may be used for drug storage system 52.

The connector 54 may be configured to retain the drug storage system 52 proximate the needle-free syringe 50, such as with the outlet 80 proximate to and fluidly connected with the injection orifice 68, as shown in FIGS. 3 and 4. The connector 54 may provide a fluid path between the outlet 80 and the injection orifice 68, which may be used for injecting the drug or fluid from the drug storage system 52 into the needle-free syringe 50. The connector 54 may include a first connecting region 88 and a second connecting region 90.

The first connecting region 88 may be configured to retain the connector 54 to the drug storage system 52, such as proximate the outlet 80. For example, the first connecting region 88 may include at least one projection or barb 92, as shown in FIGS. 3 and 4. The barbs 92 may be configured to engage corresponding recesses or openings 94 that are disposed on an adapter element 96 that is disposed on a tip 98 of the syringe 76, as shown in FIG. 4. The adapter element 96 may be retained on the tip 98 by any suitable mechanism, including friction, such as from an interference fit, welding, adhesives, or any mechanical interlocking such as threads or a bayonet-type connection. In some examples, the first connecting region 88 may be configured to directly engage the tip 98 of the syringe 76. For example, the first connecting region 88 may be frictionally and/or mechanically disposed on, or connected to, the tip 98.

The second connecting region 90 may be configured to retain the connector 54 to the needle-free syringe 50, such as proximate the injection orifice 68. For example, the second connecting region 90 may include an opening 100 that is configured to be received on an orifice tip 102 of the needle-free syringe 50, as shown in FIGS. 3 and 4. The second connecting region 90 may be frictionally retained on the needle-free syringe 50, such as due to a slight interference fit between the opening 100 and the orifice tip 102. Other suitable methods of attachment of the second connecting region 90 to the needle-free syringe 50 may include adhesives, spin and/or ultrasonic welding, or any mechanical interlocking such as threads or a bayonet-type connection.

Figure 7:
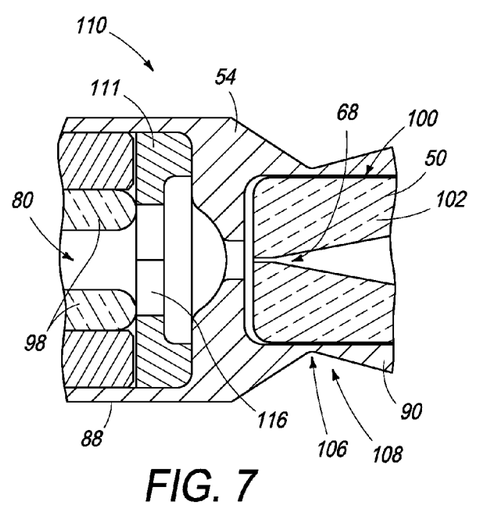
FIG. 7 is a cross section partial view of a valve region of the drug delivery system of FIG. 3, showing an illustrative example of a valve.
Figure 9:
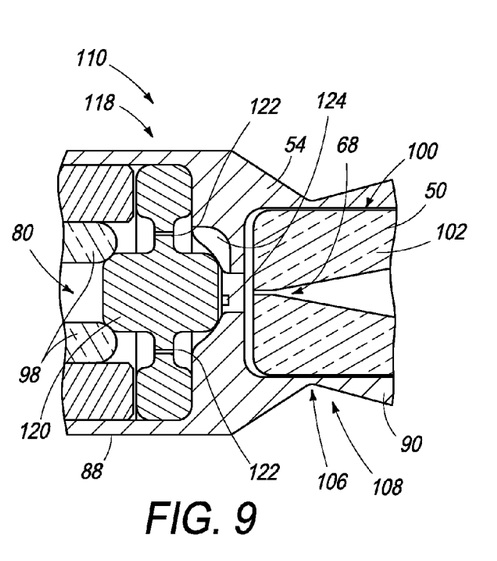
FIG. 9 is a cross section partial view the valve region of the drug delivery system of FIG. 3, showing another illustrative example of a valve.

The connector 54 may be configured to provide an easily broken or frangible connection between the needle-free syringe 50 and the drug storage system 52. Although retaining the drug storage system 52 proximate the needle-free syringe 50 while intact, such an easily broken or frangible connection may, when broken, be configured to permit or assist with separation of the drug storage system 52 from the needle-free syringe 50, as suggested in FIGS. 15 and 16. For example, the connector 54 may include a frangible region 106. As shown in FIGS. 4, 7 and 9, the frangible region 106 may be in the form of a stress riser resulting from a necked region 108 disposed between the first and second connecting regions 88, 90. As shown in FIG. 4, the necked region 108 may have a low material thickness or cross section relative to other portions of the connector 54, such as the first and second connecting regions 88, 90. When broken, the necked region 108 may permit separation of the first and second connecting regions 88, 90.

The inclusion of the frangible connection between the needle-free syringe 50 and the drug storage system 52 may configure the drug delivery system 24, the needle-free syringe 50 and/or the drug storage system 52 as single usage devices. In particular, the portions of the connector 54 remaining attached to the needle-free syringe 50 and drug delivery system 52 after the frangible region 106 has been broken may prevent and/or impede reconnection of the needle-free syringe 50 and drug delivery system 52. For example, the second connecting region 90 may remain attached to the orifice tip 102 of the needle-free syringe 50 after the frangible region 106 has been broken, which may prevent subsequently receiving another connector 54 on the orifice tip 102 of the needle-free syringe 50. In some examples, the portion of the connector 54 that remains attached to the needle-free syringe 50 and/or the needle-free syringe 50 itself may be configured to impede or prevent removal of the portion of the connector 54 without damaging the needle-free syringe 50 and/or the orifice tip 102. However, it should be understood that the remainder of the needle-free injection device 20, with possible exceptions of certain consumable parts such as gas cartridges, may be reused with another drug delivery system 24.

In some examples, the connector 54 may include a valve 110. The valve 110 may be configured to interrupt the fluid path between the outlet 80 of the storage chamber 78 and the injection orifice 68 of the needle-free syringe 50, as shown in FIG. 4. The valve 110 may be disposed between the outlet 80 and the injection orifice 68, such as proximate the outlet 80, as shown in FIG. 4. When a valve 110 is present, fluid ejected from the storage chamber 78 through the outlet 80 may open and pass through the valve 110, through the injection orifice 68, and into the injection chamber 58.

Figure 8:
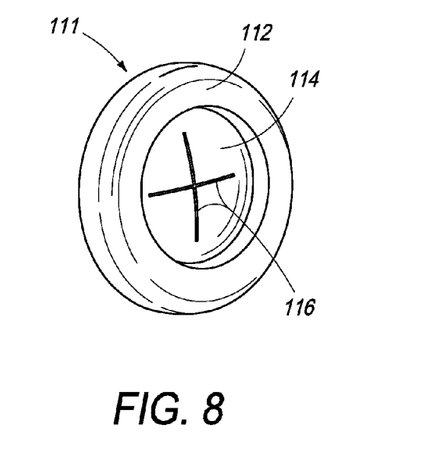
FIG. 8 is a perspective view of the valve shown in FIG. 7.
Figure 10:
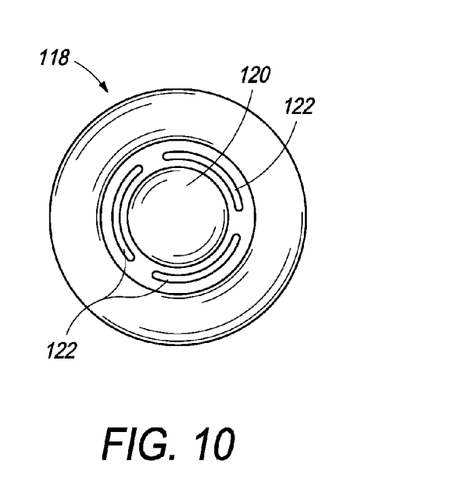
FIG. 10 is a perspective view of the valve shown in FIG. 9.

Nonexclusive illustrative examples of suitable valves 110 are shown in FIGS. 7-10. As shown in FIGS. 7 and 8, the valve 110 may include an elastomeric slit-type valve 111 having a generally circular support ring 112 that surrounds a central region. A membrane or diaphragm 114 may extend from the support ring 112 to cover the central region. The diaphragm 114 may interrupt the passage of fluid along a fluid path extending through the central region. The diaphragm 114 may include a plurality of radially oriented intersecting slits 116 that extend through the diaphragm 114 and permit the passage of fluid along a fluid path extending through the central region. As shown in FIGS. 9 and 10, the valve 110 may include a combination valve element 118, which may include a ball seal 120 and a plurality of slits 122 for the passage of fluid past the valve 110. As shown in FIG. 10, the combination valve element 118 may be associated with at least one channel 124 in the connector 54, which may assist with fluid flow around the ball seal 120. The slit-type valve element 112 and/or the combination valve element 118 may be fabricated from chlorobutyl or any other elastomeric material, such as one that is suitable for drug contact.

The power source 26 may be configured to apply a driving or injection force to the injection plunger 60, which causes the injection plunger 60 to expel the volume of fluid from the injection chamber 58 through the injection orifice 68. The power source 26 may include a compressed gas cartridge 128, a gas transfer tube 130, and a drive plunger 132. As shown in FIG. 4, the injection plunger 60 and drive plunger 132 may be configured for motion along a first axis 134, and the compressed gas cartridge 128 may be oriented along a second axis 136 that is spaced from and parallel to the first axis 134. The compressed gas cartridge 128 may be charged with a predetermined quantity of a suitable gas such as nitrogen ($N_2$ or N.sub.2) or carbon dioxide ($CO_2$ or CO.sub.2).

Figure 19:
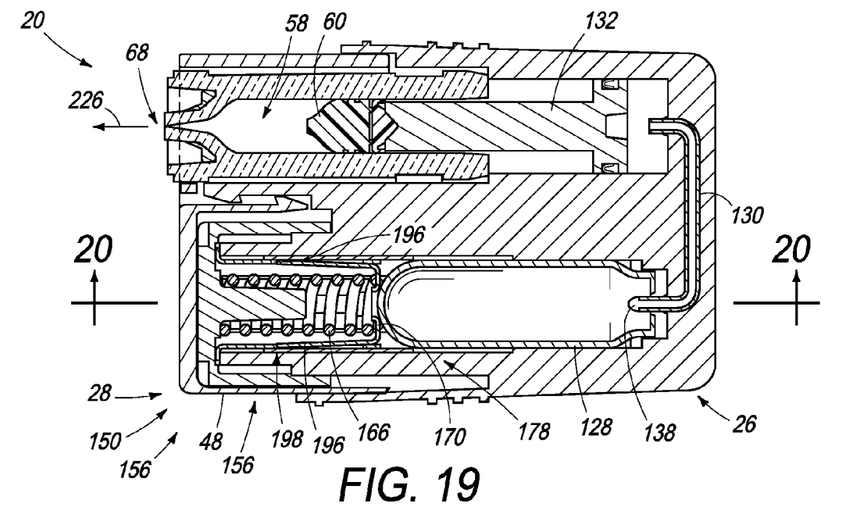
FIG. 19 is a cross section of the needle-free injection device of FIG. 1, taken generally along a line corresponding to line 4-4 in FIG. 2, shown during an injection.

The power source 26 may be configured to transfer gas from the gas cartridge 128 toward the drive plunger 132. In particular, the gas transfer tube 130 may include a piercing structure 138 disposed proximate or along the second axis 136. As shown in FIG. 19 and as will be more fully discussed below, the activation system 28 may be configured to urge the gas cartridge 128 onto the piercing structure 138 such that the piercing structure 138 perforates the gas cartridge 128. The perforation of the gas cartridge 128 allows gas from the gas cartridge 128 to flow or pass through the gas transfer tube 130 toward the drive plunger 132. The gas from the gas cartridge 128 causes the drive plunger 132 to apply the injection force to the injection plunger 60.

A pressure-resistant gas pathway may be provided between the gas cartridge 128 and the drive plunger 132. In particular, gas resistant seals 140 may be provided between respective ones of the gas cartridge 128 and the drive plunger 132 and the main body 36. As shown in FIG. 4, the gas resistant seals 140 may be O-rings or U-cup ring-type seals.

The injection plunger 60 and/or the drive plunger 132 may be configured to expel a particular volume of fluid from the injection chamber 58 through the injection orifice 68. In particular, the drive plunger 132 shown in FIG. 4 may be configured for expulsion of a relatively larger volume of fluid, such as about 1.0 mL, from the injection chamber 58. Conversely, the drive plunger 132 shown in FIG. 5, which has a greater overall length due to the inclusion of an extension region 142, may be configured for expulsion of a relatively smaller volume of fluid, such as about 0.5 mL, from the injection chamber 58. In particular, the greater overall length of the drive plunger 132 shown in FIG. 5 may limit the travel or displacement of the drive plunger 132 and the injection plunger 60 when fluid is injected into or expelled from the injection chamber 58.

The activation system 28 may be configured to selectively cause the power source 26 to apply the injection force to the injection plunger 60 by urging the gas cartridge 128 onto the piercing structure 138. The activation system 28 may include a trigger 148, a firing mechanism 150, and a trigger spring 152.

Figure 6:
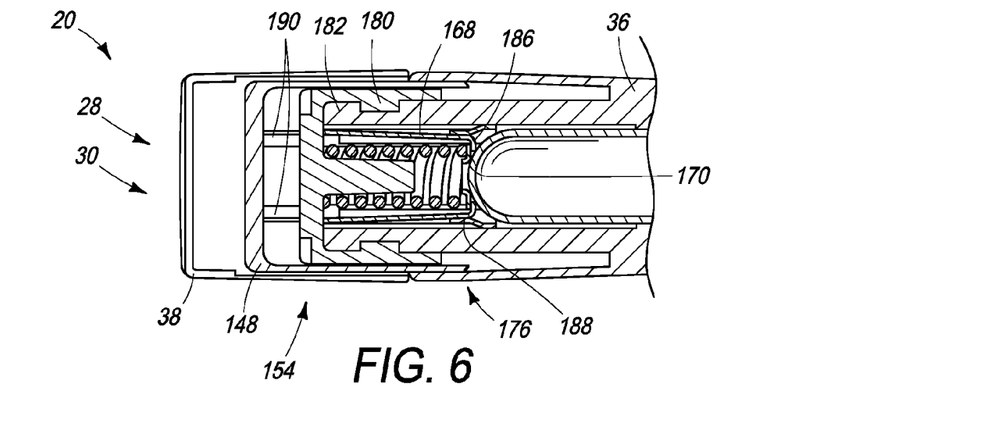
FIG. 6 is a cross section partial view of the needle-free injection device of FIG. 1, taken generally along line 6-6 in FIG. 2, with the needle-free injection device shown in the storage configuration.

The trigger 148 may be slidably mounted to the main body 36 and configured for movement from a rest position 154, as shown in FIGS. 4 and 6, toward an activating position 156, as shown in FIG. 19. Moving the trigger 148 toward the activation position 156 may cause the firing mechanism 150 to urge the gas cartridge 128 onto the piercing structure 138. The trigger 148 may be retained relative to the main body 36 by a tab 158 on the trigger 148 that is configured to engage a corresponding tab 160 on the main body, as shown in FIG. 4.

Figure 12:
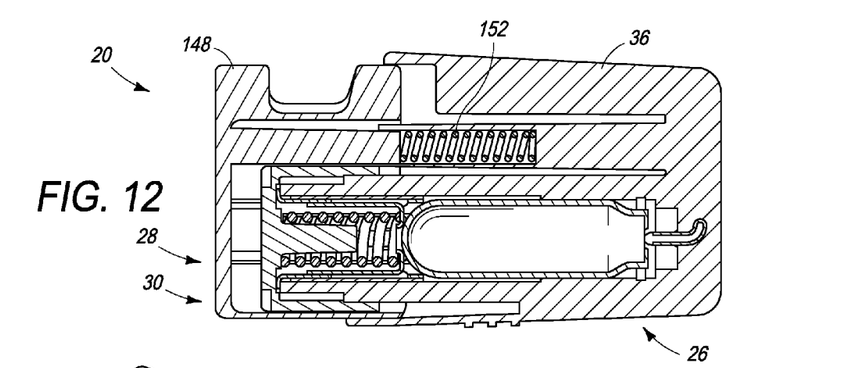
FIG. 12 is a cross section of the needle-free injection device of FIG. 1, taken generally along line 12-12 in FIG. 2, shown with the shield element and removable cap omitted.
Figure 13:
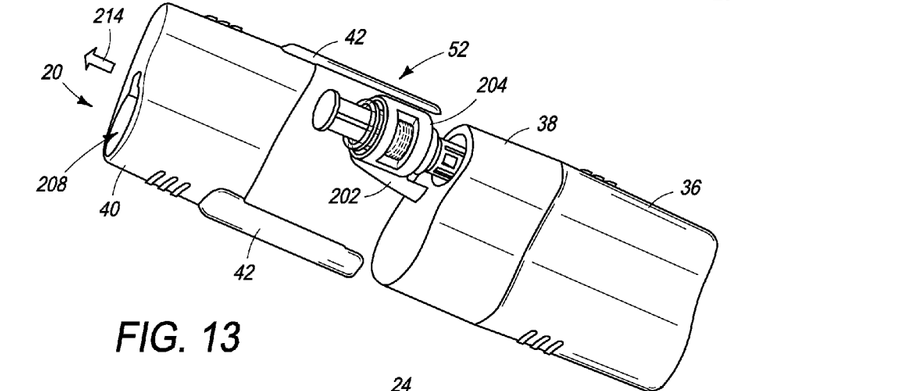
FIG. 13 is a perspective view of the needle-free injection device of FIG. 1 shown with the removable cap being removed.
Figure 14:
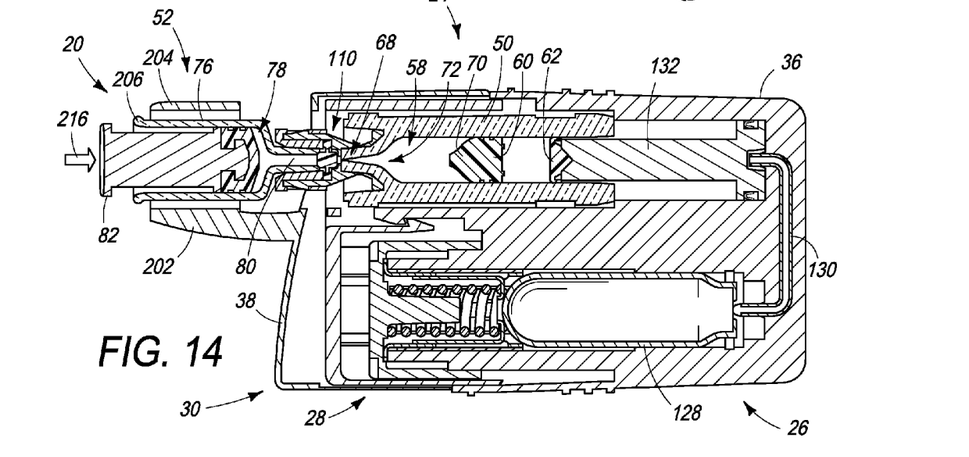
FIG. 14 is a cross section of the needle-free injection device of FIG. 1, taken generally along a line corresponding to line 4-4 in FIG. 2, shown with the removable cap removed and fluid being transferred from the drug storage system to the needle-free syringe.

The trigger spring 152 may bias the trigger 148 toward the rest position 154, as shown in FIG. 12. The trigger spring 152 may also be configured to establish an activation force level, which is the force that must be applied to the trigger 148 to cause the needle-free injection device 20 to perform an injection. The activation force level may also correspond to the force with which the needle-free injection device 20 must be held and/or pressed against an injection target, such as the skin of a patient, to effect an injection, as suggested in FIG. 18 and as will be more fully discussed below.

Figure 11:
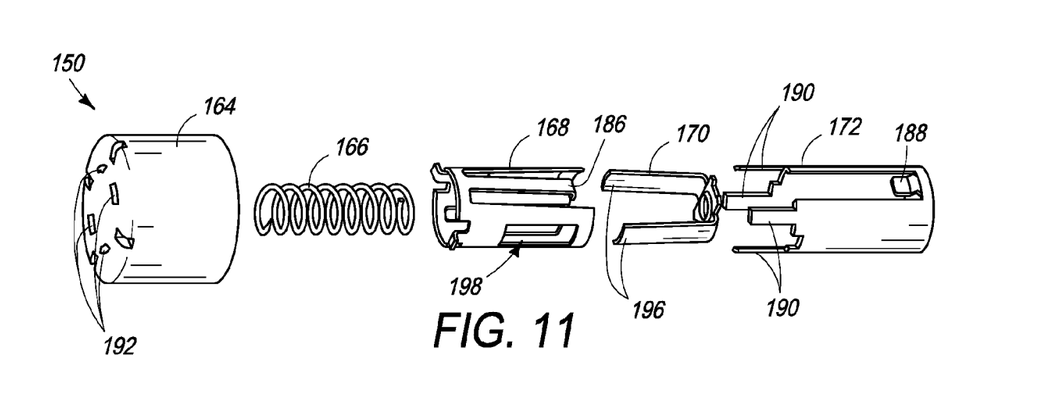
FIG. 11 is an exploded view of the firing mechanism of the needle-free injection device of FIG. 1.

The firing mechanism 150 may be configured to urge or move the gas cartridge 128 onto the piercing structure 138 in response to movement of the trigger 148 toward the activation position 156. As shown in FIGS. 4 and 11, the firing mechanism 150 may include a cap 164, a firing or driving spring 166, a driver clip or sear 168, an actuator or driver 170, and a trigger link 172. The driver 170 may be movable along the second axis 136 from a first position 176, as shown in FIG. 4, toward a second position 178, as shown in FIG. 19.

The cap 164 may be removably secured to the main body 36 by way of one or more mounting tabs 180 that are configured to engage corresponding tabs 182 on the main body 36, as shown in FIG. 6. The mounting tabs 180 and corresponding tabs 182 may be configured to provide a snap or push-on engagement between the cap 164 and the main body 36. The mounting tabs 180 and corresponding tabs 182 may additionally and/or alternatively be configured to provide a bayonet-type mounting based on rotation through less than a complete revolution, such as approximately ninety (90) degrees of rotation.

As shown in FIGS. 4 and 19, the driver spring 166 may bear against the cap 164 and the driver 170, such that the driver spring 166 may bias the driver 170 toward the second position 178. Thus, the driver spring 166 may cause the driver 170 to urge and/or move the gas cartridge 128 onto the piercing structure 138 as the driver spring 166 urges and/or moves the driver 170 toward the second position 178.

Figure 20:
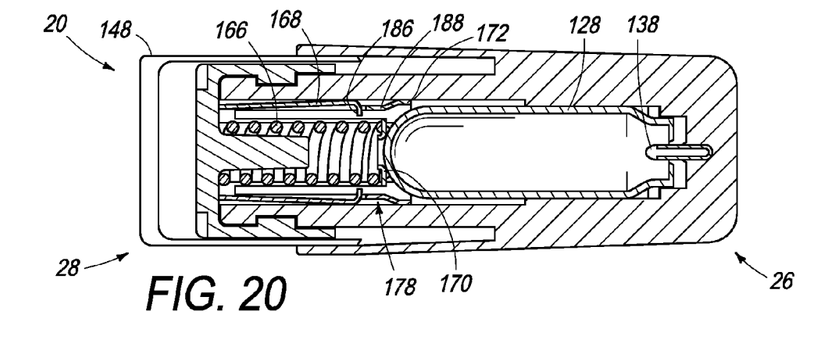
FIG. 20 is a cross section of the needle-free injection device of FIG. 1, taken generally along a line corresponding to line 20-20 in FIG. 19, shown after an injection, with the trigger released.

The sear 168 may be configured to selectively retain the driver 170 in the first position 176. In particular, the sear 168 may include a pair of inwardly projecting sear tabs 186 that are configured to engage and retain the driver 170 in the first position 176, as shown in FIG. 6. The inwardly projecting sear tabs 186 may be outwardly biased to release the driver 170, as shown in FIG. 20. A pair of trigger link tabs 188 on the trigger link 172 may retain the inwardly projecting sear tabs 186 in engagement with the driver 170 when the trigger 148 is in the rest position, as shown in FIG. 6.

The trigger link 172 may include a plurality of fingers 190, which are configured to extend through corresponding openings 192 in the cap 164, as shown in FIG. 11. The fingers 190 may bear against the trigger 148 when the trigger is in the rest position 154, as shown in FIGS. 4 and 6, such that movement of the trigger 148 toward the activating position 156 displaces the trigger link 172 such that the trigger link tabs 188 release the sear tabs 186, which may then spread apart and release the driver 170, as shown in FIG. 20.

The driver 170 may include a pair of latches 196 that are configured to retain the driver in the second position 178. The latches 196 may be outwardly biased such that the latches may engage a corresponding opening 198 on the sear 168 when the driver is in the second position 178, as shown in FIG. 19. When the driver 170 is in the first position 176 and/or between the first and second positions 176, 178, the latches 196 may be inwardly displaced by the sear 168, as shown in FIG. 4. Further, by retaining the driver 170 in the second position 178, the latches 196 may also retain the gas cartridge 128 on the piercing structure 138, as shown in FIG. 19.

The activation preventing or disabling element 30 may be configured to prevent the power source 26 from applying the injection force to the injection plunger 60 when the drug storage system 52 is connected to the needle-free syringe 50. In particular, when the drug storage system 52 is connected to the needle-free syringe 50, the disabling element 30 may be configured to prevent the activation system 28 from urging the gas cartridge 128 onto the piercing structure 138. For example, the disabling element 30 may be retained on the main body 36 by the drug storage system 52 when the drug storage system 52 is connected to the needle-free syringe 50. When retained on the main body 36, the disabling element 30 may impede or prevent movement of the trigger 148 toward the activation position 156, which may impede or prevent the driver 170 from urging the gas cartridge 128 onto the piercing structure 138.

Conversely, the disabling element 30 may be configured to permit or otherwise enable application of the injection force by the power source 26 to the injection plunger 60 when the drug storage system 52 is disconnected from the needle-free syringe 50. In particular, when the connector 54 has been broken and the drug storage system 52 has been removed from the needle-free syringe 50, the disabling element 30 may be configured or configurable to permit the activation system 28 to urge the gas cartridge 128 onto the piercing structure 138. For example, when the drug storage system 52 has been removed from the needle-free syringe 50, the disabling element 30 may be removed from the main body 36. When removed from the main body 36, the disabling element 30 may not interfere with movement of the trigger 148 toward the activation position 156.

The disabling element 30 may include and/or be in the form of a cap or shield element 38 that is removably mounted to the main body 36. The shield element 38 may be configured to impede or prevent access to the activation system 28 when the shield element 38 is mounted to the main body 36. Thus, when mounted to the main body 36, the shield element 38 may impede or prevent the activation system 28 from urging the gas cartridge 128 onto the piercing structure 138. For example, as shown in FIGS. 4, 6 and 13-14, the shield element 38 may impede or prevent movement of the trigger 148 toward the activation position 156 by impeding or preventing access to the trigger 148.

The shield element 38 may configured such that it may not be removed from the main body 36 when the drug storage system 52 is connected to the needle-free syringe 50. For example, as shown in FIG. 4, the shield element 38 may include an arm 202 that supports a collar 204. The collar 204 may extend around the syringe 76 of the drug storage system 52. The collar 204 may be configured for a relatively close fit to the syringe 76, and a lip or rim 206 on the syringe 76 may be larger than the collar 204. The drug storage system 52 may thus prevent removal of the shield element 38 from the main body 36 when the drug storage system 52 is connected to the needle-free syringe 50 because the collar 204 may be unable to pass over the rim 206 on the syringe 76.

Figure 16:
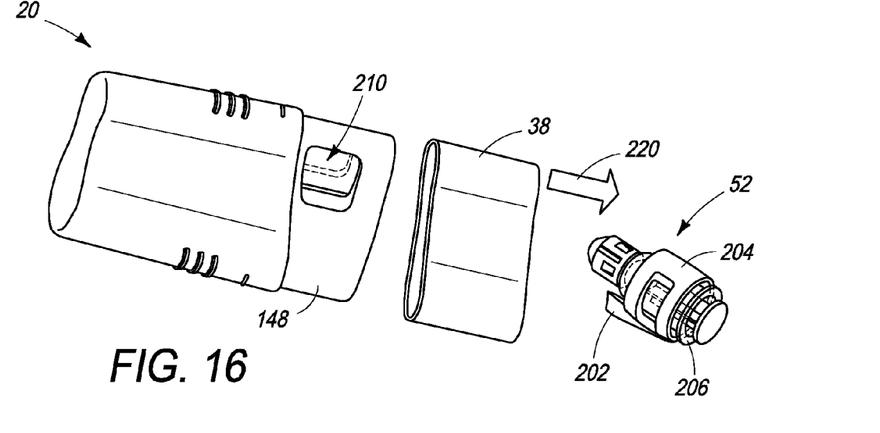
FIG. 16 is a perspective view of the needle-free injection device of FIG. 1 shown with the shield element being removed.

The arm 202 may be frangibly connected to the shield element 38. Thus, breaking the frangible connection between the needle-free syringe 50 and the drug storage system 52 may concurrently break the frangible connection between the arm 202 and the shield element 38, as shown in FIG. 16. Once the frangible connection between the needle-free syringe 50 and the drug storage system 52 and the frangible connection between the arm 202 and the shield element 38 have been broken and disconnected, shield element 38 may be removed from the main body 36, as shown in FIG. 16.

Figure 15:
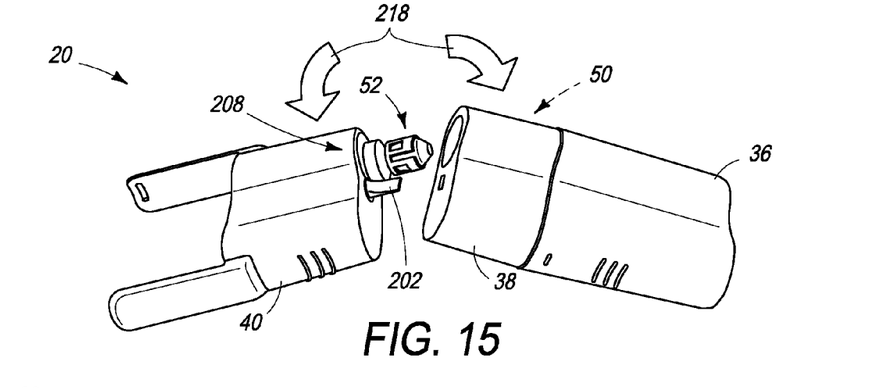
FIG. 15 is a perspective view of the needle-free injection device of FIG. 1 shown with the connector being broken.

In some examples, the removable cap 40 may be configured to assist with breaking the frangible connections between the needle-free syringe 50 and the drug storage system 52 and between the arm 202 and the shield element 38. For example, the removable cap 40 may include a socket 208, as shown in FIGS. 1, 2 and 4. The socket 208 may be configured to engage the drug storage system 52 and/or the arm 202, as shown in FIG. 15, which may provide additional leverage for breaking the frangible connections.

In some examples, one or more components of the needle-free injection device 20 may be configured to provide an indication regarding the condition of the needle-free injection device 20 and/or the drug delivery system 24, such as whether fluid is present in, or has been injected into, the injection chamber 58 or whether the injection plunger 60 has expelled a volume of fluid from the injection chamber 58. For example, the needle-free syringe 50 and/or the syringe 76 may be at least partially transparent. Further, the main body 36 and/or the trigger 148, as shown in FIGS. 16 and 18, may include at least one opening or window 210 through which the needle-free syringe 50 may be visible.

Figure 17:
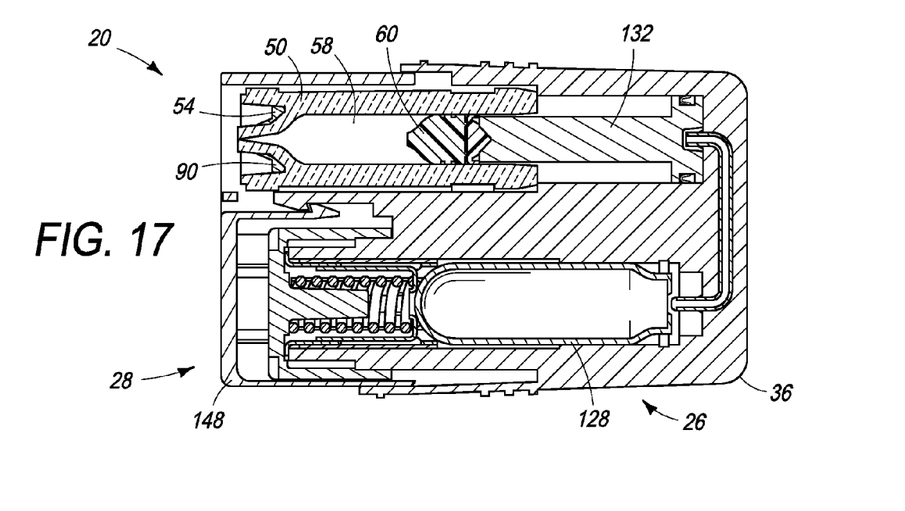
FIG. 17 is a cross section of the needle-free injection device of FIG. 1, taken generally along a line corresponding to line 4-4 in FIG. 2, shown in a primed condition.

A user may use the needle-free injection device 20 to perform or make a needle-free injection. The needle-free injection device 20 may be stored and/or distributed with the removable cap 40 attached to the main body 36, as shown in FIGS. 1 and 4. The drug or fluid may be stored within the storage chamber 78 of the drug storage system 52. The removable cap 40 may be removed, as indicated by the arrow 214 in FIG. 13. A drug or fluid may be transferred from the storage chamber 78 of the drug storage system 52 to the injection chamber 58 of the needle-free syringe 50 by depressing the plunger 82, as indicated by the arrow 216 in FIG. 14. Depressing the plunger 82 may eject the drug or fluid from the storage chamber 78, through the outlet 80, through the valve 110, if present, and through the injection orifice 68 and into the injection chamber 58. The frangible connections between the needle-free syringe 50 and the drug storage system 52 and between the arm 202 and the shield element 38 may be broken, as generally indicated by the arrows 218 in FIG. 15. The socket 208 on the removable cap 40 may be used to engage the drug storage system 52 and/or the arm 202. The shield element 38 may be slid from the needle-free injection device 20 and discarded along with the drug storage system 52, as suggested by the arrow 220 in FIG. 16. The needle-free injection device 20 may then be in a primed or ready-to-inject condition, with the injection chamber 58 charged or filled with a drug or fluid and the drug storage system 52 and shield element 38 removed, as shown in FIG. 17.

Figure 18:
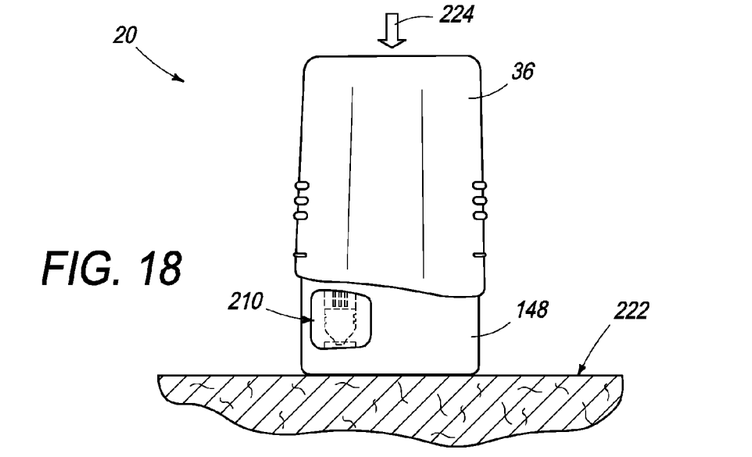
FIG. 18 is a perspective view illustrating performance of an injection with the needle-free injection device of FIG. 1.

The primed needle-free injection device 20 may be urged or pressed against a target surface 222, such as an arm or other suitable location, as indicated by the arrow 224 in FIG. 18. When the primed needle-free injection device 20 is pressed against the target surface 222 with sufficient force to overcome the bias induced by the trigger spring 152, the trigger 148 moves toward the activation position 156, as shown in FIG. 19. Moving the trigger 148 toward the activation position 156 moves the trigger link 172 such that the trigger link tabs 188 release the sear tabs 186, which release the driver 170. The driving spring 166 moves the driver 170 toward its second position 178, which moves the gas cartridge 128 onto the piercing structure 138 and allows the latches 196 to engage the sear 168 to retain the gas cartridge 128 on the piercing structure 138. The gas from the gas cartridge 128 causes the drive plunger 132 to apply the driving or injection force to the injection plunger 60. The driving or injection force causes the injection plunger 60 to expel a volume of fluid from the injection chamber 58 and through the injection orifice 68, as indicated by the arrow 226 in FIG. 19.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the disclosure includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A needle-free injection device, comprising:
a drug delivery system, including:
a needle-free syringe having an injection chamber and a plunger slidably disposed within the injection chamber, wherein the injection chamber includes an injection orifice, and the plunger is configured to expel a volume of fluid from the injection chamber through the injection orifice, and
a drug storage system having a storage chamber and an outlet, wherein the drug storage system is frangibly connected to the needle-free syringe with the outlet proximate to and fluidly connected with the injection orifice, and the drug storage system is configured to inject a fluid from the storage chamber through the outlet, through the injection orifice, and into the injection chamber;
a power source configured to apply an injection force to the plunger to expel the volume of fluid from the injection chamber through the injection orifice;
an activation system configured to selectively cause the power source to apply the injection force, wherein the activation system includes an actuator that is movable between a first position and a second position, and in the second position the actuator is configured to cause the power source to apply the injection force; and
a disabling element configured to prevent movement of the actuator from the first position toward the second position to prevent the activation system from causing the power source to apply the injection force when the drug storage system is frangibly connected to the needle-free syringe, wherein the disabling element is configured to permit application of the injection force when the drug storage system is disconnected from the needle-free syringe, and the disabling element includes a shield element removably disposed on the needle-free injection device and configured to impede access to the activation system when the shield element is disposed on the needle-free injection device.

2. The needle-free injection device of claim 1, wherein the shield element is configured such that the drug storage system prevents removal of the shield element from the needle-free injection device when the drug storage system is connected to the needle-free syringe, and the shield element is configured such that disconnection of the drug storage system from the needle-free syringe permits removal of the shield element from the needle-free injection device.

3. The needle-free injection device of claim 1, wherein the shield element is configured to permit injection of fluid from the storage chamber of the drug storage system and into the injection chamber of the needle-free syringe while the shield element is disposed on the needle-free injection device.

4. The needle-free injection device of claim 1, wherein the injection chamber of the needle-free syringe comprises a thermoplastic material.

5. The needle-free injection device of claim 1, wherein the power source includes a compressed gas cartridge, the compressed gas cartridge is oriented along a first axis, and the plunger is configured for motion along a second axis spaced from and parallel to the first axis.

6. A needle-free injection device, comprising:
a drug delivery system, including:
a needle-free syringe having an injection chamber and a plunger slidably disposed within the injection chamber, wherein the injection chamber includes an injection orifice and the plunger is configured to expel a volume of fluid from the injection chamber through the injection orifice,
a drug storage system having a storage chamber and an outlet, wherein the storage chamber is configured to inject a fluid from the storage chamber through the outlet, through the injection orifice, and into the injection chamber, and
a frangible connector configured to retain the drug storage system proximate the needle-free syringe with the outlet proximate to and fluidly connected with the injection orifice;
a power source configured to apply an injection force to the plunger to expel the volume of fluid from the injection chamber through the injection orifice;
an activation system configured to selectively cause the power source to apply the injection force, wherein the activation system includes a driver that is movable from a first position toward a second position, the driver is biased toward the second position, the driver is releasably retained in the first position, and in the second position the driver is configured to cause the power source to apply the injection force; and
an activation preventing element configured to prevent the activation system from causing the power source to apply the injection force when the frangible connector is retaining the drug storage system proximate the needle-free syringe, wherein the activation preventing element is configured to permit the activation system to cause the power source to apply the injection force when the frangible connector has been broken, and the activation preventing element includes a shield element removably disposed on the needle-free injection device and configured to prevent movement of the driver from the first position toward the second position when the shield element is disposed on the needle-free injection device.

7. The needle-free injection device of claim 6, wherein the frangible connector is configured to permit separation of the drug storage system from the needle-free syringe when the frangible connection has been broken.

8. The needle-free injection device of claim 6, wherein the shield element is configured such that the drug storage system prevents removal of the shield element from the needle-free injection device when the frangible connector is retaining the drug storage system proximate the needle-free syringe, and the shield element is configured such that breaking the frangible connector and separating the drug storage system from the needle-free syringe permits removal of the shield element from the needle-free injection device.

9. The needle-free injection device of claim 6, wherein:
the plunger is configured for motion along a first axis;
the power source includes a compressed gas cartridge and a gas transfer tube, the compressed gas cartridge is oriented along a second axis spaced from and parallel to the first axis, and the gas transfer tube includes a piercing structure disposed on the second axis;
the driver is movable along the second axis from the first position toward the second position;
the driver is configured to urge the gas cartridge onto the piercing structure as the driver moves toward the second position; and
the gas transfer tube is configured to transfer gas from the gas cartridge toward the plunger such that the gas urges the plunger to expel the volume of fluid from the injection chamber through the injection orifice.

10. The needle-free injection device of claim 9, wherein the driver includes at least one latch configured to retain the driver in the second position.

11. A needle-free injection device, comprising:
a drug delivery system, including:
a needle-free syringe having an injection chamber and a plunger slidably disposed within the injection chamber, wherein the injection chamber includes an injection orifice and the plunger is configured to expel a volume of fluid from the injection chamber through the injection orifice,
a drug storage system having a storage chamber and an outlet, wherein the storage chamber is configured to eject a fluid from the storage chamber through the outlet, through the injection orifice, and into the injection chamber, and
a frangible connector configured to retain the drug storage system proximate the needle-free syringe with the outlet proximate to and fluidly connected with the injection orifice, wherein the frangible connector includes a valve disposed between the outlet and the injection orifice, and the fluid ejected from the storage chamber through the outlet opens the valve and passes through the valve, through the injection orifice, and into the injection chamber;

a power source configured to apply an injection force to the plunger to expel the volume of fluid from the injection chamber through the injection orifice;
an activation system configured to selectively cause the power source to apply the injection force; and
an activation preventing element configured to prevent the activation system from causing the power source to apply the injection force when the frangible connector is retaining the drug storage system proximate the needle-free syringe, wherein the activation preventing element is configured to permit the activation system to cause the power source to apply the injection force when the frangible connector has been broken.

12. A drug delivery system for a needle-free injection device, the drug delivery system comprising:
a needle-free syringe including an injection chamber and an injection plunger slidably disposed within the injection chamber, wherein the injection chamber includes an injection orifice, and the injection plunger is configured to expel a volume of fluid from the injection chamber through the injection orifice;
a drug storage system including a storage chamber, an outlet and an ejection plunger, wherein the ejection plunger is configured to eject a fluid from the storage chamber through the outlet; and
a connector configured to retain the drug storage system proximate the needle-free syringe with the outlet proximate the injection orifice, the connector including:
a first connecting region configured to retain the connector to the drug storage system proximate the outlet,
a second connecting region configured to retain the connector to the needle-free syringe proximate the injection orifice,
a fluid path configured to fluidly connect the outlet and the injection orifice,
a valve configured to interrupt the fluid path proximate the outlet, wherein the fluid ejected from the storage chamber through the outlet passes through the valve, through the injection orifice, and into the injection chamber, and
a stress riser configured to assist with separation of the first and second connecting regions and to permit separation of the drug storage system from the needle-free syringe when the connector is broken proximate the stress riser.

13. The drug delivery system of claim 12, wherein the stress riser includes a frangible region disposed intermediate the first and second connecting regions, the connector is configured to retain the drug storage system proximate the needle-free syringe while the frangible region remains unbroken, and the connector is configured such that breaking the frangible region permits separation of the drug storage system from the needle-free syringe.

14. The drug delivery system of claim 12, wherein the injection chamber of the needle-free syringe comprises a thermoplastic material and the storage chamber of the drug storage system comprises a borosilicate glass.

15. The drug delivery system of claim 12, wherein the valve includes a membrane configured to interrupt the fluid path and a plurality of radially oriented intersecting slits through the membrane.

* * * * *